United States Patent
Sakakibara et al.

(10) Patent No.: US 10,228,346 B2
(45) Date of Patent: Mar. 12, 2019

(54) GAS SENSOR ELEMENT AND GAS SENSOR

(71) Applicant: NGK INSULATORS, LTD., Nagoya-shi, Aichi (JP)

(72) Inventors: Hironori Sakakibara, Kasugai (JP); Shuichi Ozawa, Nagoya (JP); Hiroki Fujita, Kasugai (JP); Shinsaku Maeda, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 256 days.

(21) Appl. No.: 14/956,949

(22) Filed: Dec. 2, 2015

(65) Prior Publication Data

US 2016/0161445 A1 Jun. 9, 2016

(30) Foreign Application Priority Data

Dec. 4, 2014 (JP) .................................. 2014-245661
Nov. 30, 2015 (JP) .................................. 2015-233562

(51) Int. Cl.
| | | |
|---|---|---|
| *G01N 27/407* | (2006.01) | |
| *G01N 27/12* | (2006.01) | |
| *G01N 27/419* | (2006.01) | |
| *G01N 27/409* | (2006.01) | |
| *G01N 27/416* | (2006.01) | |

(52) U.S. Cl.
CPC ......... *G01N 27/419* (2013.01); *G01N 27/409* (2013.01); *G01N 27/4075* (2013.01); *G01N 27/4077* (2013.01); *G01N 27/4166* (2013.01)

(58) Field of Classification Search
CPC ............ G01N 27/419; G01N 27/4075; G01N 27/4077; G01N 27/409; G01N 27/4166; G01N 27/125; G01N 27/304
See application file for complete search history.

(56) References Cited

U.S. PATENT DOCUMENTS

| | | |
|---|---|---|
| 5,271,821 A | 12/1993 | Ogasawara et al. |
| 5,766,434 A | 6/1998 | Fujii et al. |
| 2002/0008025 A1 | 1/2002 | Fujii et al. |
| 2004/0007462 A1 | 1/2004 | Hotta et al. |

(Continued)

FOREIGN PATENT DOCUMENTS

| | | |
|---|---|---|
| EP | 2363707 A1 | 9/2011 |
| EP | 2372358 A1 | 10/2011 |

(Continued)

OTHER PUBLICATIONS

The Extended European Search Report for the corresponding European patent application No. 15197867.3 dated May 3, 2016.

(Continued)

*Primary Examiner* — Susan D Leong
(74) *Attorney, Agent, or Firm* — Global IP Counselors, LLP

(57) ABSTRACT

A sensor element includes a sensor element main body a including an oxygen ion-conductive solid electrolyte layer and a porous protective layer covering at least part of the sensor element main body. Then, the porous protective layer has the value of the number of interfaces in a unit thickness direction, which is the number of particle interfaces of constituent particles every 100 μm in the thickness direction, of 15 or more and 250 or less.

15 Claims, 4 Drawing Sheets

(56) References Cited

U.S. PATENT DOCUMENTS

| | | | |
|---|---|---|---|
| 2007/0095662 A1* | 5/2007 | Suzuki | G01N 27/4071 |
| | | | 204/424 |
| 2007/0170057 A1* | 7/2007 | Kobayashi | G01N 27/4071 |
| | | | 204/424 |
| 2008/0156644 A1 | 7/2008 | Suzuki et al. | |
| 2009/0188620 A1 | 7/2009 | Okuda et al. | |
| 2009/0255812 A1 | 10/2009 | Yoshida et al. | |
| 2010/0155240 A1 | 6/2010 | Matsuoka et al. | |
| 2011/0094883 A1 | 4/2011 | Ito et al. | |
| 2012/0248071 A1 | 10/2012 | Ikoma | |
| 2013/0192988 A1 | 8/2013 | Shiono et al. | |
| 2014/0102170 A1 | 4/2014 | Kato | |
| 2014/0130572 A1 | 5/2014 | Otsuka et al. | |
| 2014/0291150 A1 | 10/2014 | Otsuka et al. | |

FOREIGN PATENT DOCUMENTS

| | | |
|---|---|---|
| JP | 3766572 B2 | 2/2006 |
| JP | 2008-164411 A | 7/2008 |
| JP | 2009-175099 A | 8/2009 |
| JP | 2012-210637 A | 11/2012 |
| JP | 2013-54025 A | 3/2013 |
| WO | 2013/005491 A1 | 1/2013 |

OTHER PUBLICATIONS

Vardelle et al., "Influence of Particle Parameters at Impact on Splat Formation and Solidification in Plasma Spraying Processes", Journal of Thermal Spray Technology, Mar. 1, 1995, p. 50-58, vol. 4 No. 1, ASM International, US.

Bianch et al., "Splat formation and cooling of plasma-sprayed zirconia", Thin Solid Films, Aug. 1, 1997, pp. 35-47, vol. 305 No. 1-2, Elesevier-Sequoia S.A., Lausanne, Switzerland.

Kulkarni et al., "Processing effects on porosity-property correlations in plasma sprayed yttria-stabilized zirconia mating", Material Science and Engineering A: Structural Materials: Properties, Microstructure and Processing, Oct. 25, 2003, pp. 100-111, vol. 359, Elesevier B.V., Neatherland.

* cited by examiner

Gas to be Measured →

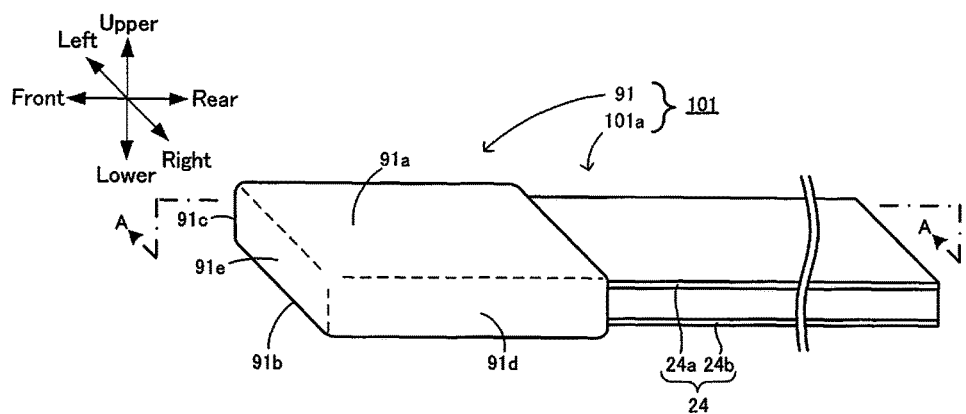
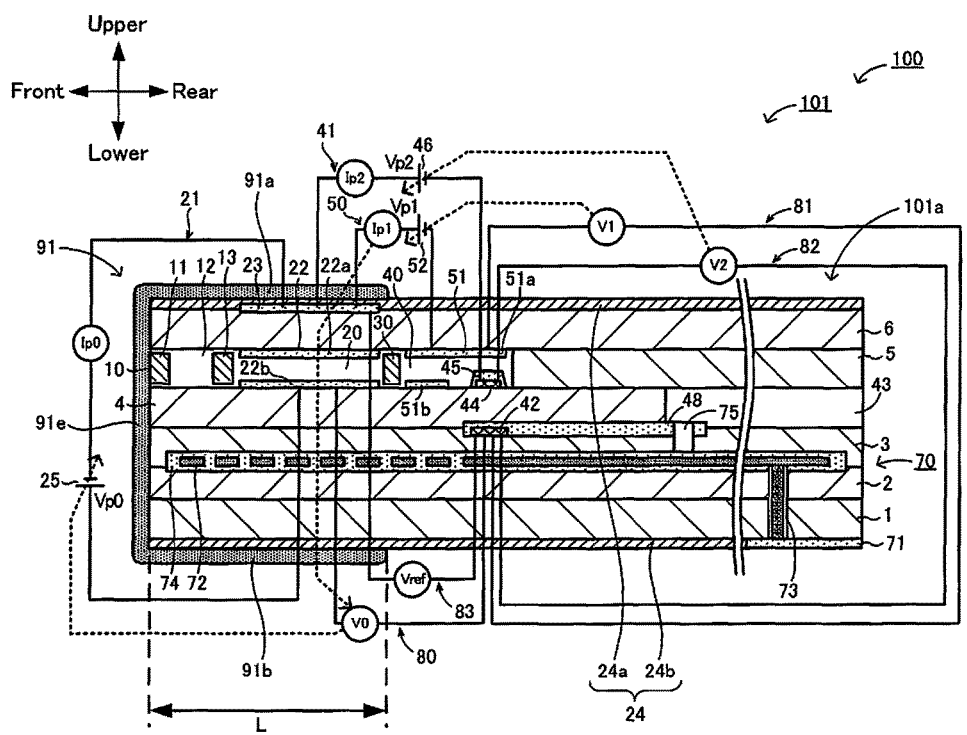

GAS SENSOR ELEMENT AND GAS SENSOR

BACKGROUND OF THE INVENTION

1. Field of the Invention

The present invention relates to a gas sensor element and a gas sensor.

2. Description of the Related Art

To date, gas sensors including sensor elements for detecting the concentrations of predetermined gases, e.g., NOx, in gases to be measured, such as automobile exhaust gases, are known. It is also known that a porous protective layer is formed on the surface of the sensor element in such a gas sensor. For example, PTLs 1 and 2 describe a technique to form the porous protective layer by causing heat-resistant particles, e.g., alumina, to adhere to the surface of a sensor element by plasma spraying. It is mentioned that, for example, cracking or the like of the sensor element due to adhesion of moisture in a gas to be measured can be suppressed by formation of the porous protective layer.

CITATION LIST

Patent Literature

JP 2013-54025 A
JP 3766572 B

SUMMARY OF THE INVENTION

The temperature in the operation of the sensor element of such a gas sensor is usually high (for example, 800° C.), and it is desirable that cracking of the sensor element due to rapid cooling caused by adhesion of moisture be further suppressed.

The present invention was made so as to solve such problems and a main object is to improve waterproofing performance of the gas sensor element.

In the present invention, the following measures are adopted so as to achieve the above-described main object.

A first gas sensor element according to the present invention includes:

an element main body including an oxygen ion-conductive solid electrolyte layer; and a protective layer covering at least part of the element main body and having the value of the number of interfaces in a unit thickness direction, which is the number of particle interfaces of constituent particles every 100 μm in the thickness direction, of 15 or more and 250 or less.

In the first gas sensor element, at least part of the element main body is covered with the protective layer. Here, as the number of interfaces in a unit thickness direction, which is the number of particle interfaces of constituent particles every 100 μm in the thickness direction, of the protective layer increases, occurrence of heat conduction in the thickness direction of the protective layer tends to become difficult. That is, cooling of the element main body in the case where moisture adheres to the surface of the protective layer tends to be suppressed. The reason for this is considered to be that the heat conduction between the constituent particles does not occur easily as compared with the heat conduction in the constituent particle. Then, the value of the number of interfaces in a unit thickness direction is 15 or more and, thereby, an effect of suppressing cooling of the element main body, that is, an effect of improving the waterproofing performance of the gas sensor element, is obtained. In this regard, as the number of interfaces in a unit thickness direction increases, the number of constituent particles per unit thickness increases and the gas to be measured does not easily pass through the protective layer to reach the element main body. If the value of the number of interfaces in a unit thickness direction is 250 or less, the gas can pass through the protective layer. In the first gas sensor element, the thickness of the above-described protective layer may be 50 μm or more, or the thickness of the above-described protective layer may be 100 μm or more. Also, the above-described protective layer may have the value of the number of interfaces in a unit thickness direction of 17 or more. The above-described protective layer may have the value of the number of interfaces in a unit thickness direction of 200 or less, 150 or less, 100 or less, or 50 or less.

A second gas sensor element according to the present invention includes:

an element main body including an oxygen ion-conductive solid electrolyte layer; and a protective layer covering at least part of the element main body and having the value of the ratio of the number of interfaces (=the number of interfaces in a unit surface direction/the number of interfaces in a unit thickness direction) of the number of interfaces in a unit surface direction, which is the number of particle interfaces of constituent particles every 100 μm in the surface direction perpendicular to the thickness direction, to the number of interfaces in a unit thickness direction, which is the number of particle interfaces of constituent particles every 100 μm in the thickness direction, of more than 0 and 0.7 or less.

In the second gas sensor element, at least part of the element main body is covered with the protective layer. Here, as the ratio of the number of interfaces (=the number of interfaces in a unit surface direction/the number of interfaces in a unit thickness direction) of the protective layer decreases, heat conduction in the surface direction (direction perpendicular to the thickness direction) of the protective layer tends to occur as compared with heat conduction in the thickness direction of the protective layer. The reason for this is considered to be that the heat conduction between the constituent particles does not occur easily as compared with the heat conduction in the constituent particle. Consequently, as the ratio of the number of interfaces decreases, cooling of only part of the element main body in the case where moisture adheres to the surface of the protective layer tends to be suppressed. Then, the ratio of the number of interfaces is 0.7 or less and, thereby, an effect of suppressing occurrence of cracking due to rapid cooling of only part of the element main body, that is, an effect of improving the waterproofing performance of the gas sensor element, is obtained. In this regard, the value of the ratio of the number of interfaces may be 0.6 or less, and the value is preferably 0.4 or less, or 0.3 or less. The value of the ratio of the number of interfaces may be 0.15 or more. In addition, in the second gas sensor element, the thickness of the above-described protective layer may be 50 μm or more, or the thickness of the above-described protective layer may be 100 μm or more. Also, the above-described value of the number of interfaces in a unit thickness direction may be 15 or more or the value may be 250 or less. The above-described value of the number of interfaces in a unit surface direction may be 5 or more, the value may be 10.5 or less, or the value may be 10 or less.

In the first and second gas sensor elements, the value of the number of interfaces in a unit thickness direction of the above-described protective layer may be 30 or more. Consequently, the waterproofing performance of the gas sensor element is further improved.

In the first and second gas sensor elements according to the present invention, the thickness of the above-described protective layer may be 500 μm or less. Here, in the case where the thickness of the protective layer is 500 μm or less that is relatively small, the waterproofing performance of the gas sensor element tends to be insufficient. The waterproofing performance of the first gas sensor element according to the present invention can be improved in the case where the value of the number of interfaces in a unit thickness direction of the protective layer is 15 or more. Therefore, application of the present invention to such a relatively thin protective layer is highly significant. Likewise, the waterproofing performance of the second gas sensor element according to the present invention can be improved in the case where the ratio of the number of interfaces is 0.7 or less. Therefore, application of the present invention to such a relatively thin protective layer is highly significant.

In the first and second gas sensor elements according to the present invention, the above-described protective layer may contain ceramic particles as the above-described constituent particles. The ceramic particles are suitable for the protective layer of the gas sensor element from the viewpoint of at least one of the strength, the heat resistance, and the corrosion resistance.

In the first and second gas sensor elements according to the present invention, the above-described protective layer may contain particles of at least one of alumina, zirconia, spinel, cordierite, titania, and magnesia as the above-described constituent particles. These materials have high heat resistance and, therefore, are suitable for the protective layer of the gas sensor element.

In the first and second gas sensor elements according to the present invention, the above-described element main body has long lengths of rectangular parallelepiped shape, and the above-described protective layer may cover one end surface in the longitudinal direction of the above-described element main body and regions of four surfaces perpendicular to the one end surface to the position at a distance L in the above-described longitudinal direction of the element main body from the one end surface side (where 0<distance L<length in the longitudinal direction of the element main body). Since the protective layer covers five surfaces as described above, an effect of protecting the element main body by the protective layer is enhanced as compared with the case where, for example, the protective layer covers only four surfaces at most.

A gas sensor according to the present invention includes:

the gas sensor element according to any one of the above-described aspects.

The gas sensor includes the gas sensor element according to any one of the above-described aspects of the first and second gas sensor elements according to the present invention. Consequently, the same effects as those of the above-described first and second gas sensor elements according to the present invention, for example, the effect of improving the waterproofing performance of the gas sensor element, are obtained. In this case, in the above-described gas sensor element, the above-described element main body may have a long length of rectangular parallelepiped shape. Also, the gas sensor according to the present invention may include a fixing member for fixing the above-described gas sensor element and a protective cover for covering one end surface in the longitudinal direction of the above-described gas sensor element.

BRIEF DESCRIPTION OF THE DRAWINGS

FIG. 2 is a perspective view schematically illustrating an example of the configuration of a sensor element 101.

FIG. 3 is a sectional view along a line A-A in FIG. 2.

FIG. 4 is a conceptual diagram illustrating the manner of measurement of the number of interfaces in a unit thickness direction and the like.

DETAILED DESCRIPTION OF THE INVENTION

Figure 1:
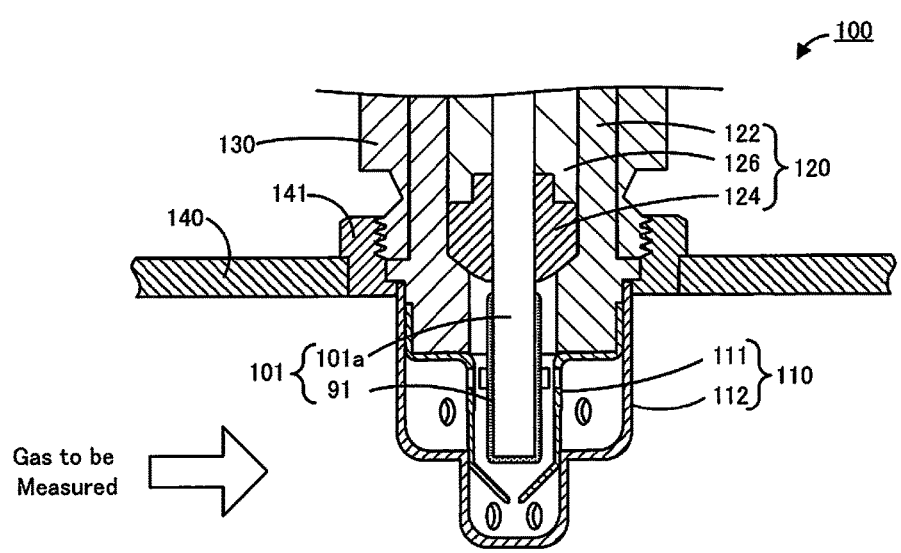
FIG. 1 is a vertical sectional view of a gas sensor 100.

Next, embodiments according to the present invention will be described with reference to the drawings. FIG. 1 is a vertical sectional view of a gas sensor 100 according to an embodiment of the present invention. FIG. 2 is a perspective view schematically illustrating an example of the configuration of a sensor element 101. FIG. 3 is a sectional view along a line A-A in FIG. 2. In this regard, the sensor element 101 has long lengths of rectangular parallelepiped shape. The longitudinal direction of the sensor element 101 (right/left direction in FIG. 2) is specified to be a front/rear direction and the thickness direction of the sensor element 101 (vertical direction in FIG. 2) is specified to be a vertical direction. Also, the width direction of the sensor element 101 (direction perpendicular to the front/rear direction and the vertical direction) is specified to be a right/left direction. In this regard, the structure of the gas sensor 100 illustrated in FIG. 1 is known and is described in, for example, Japanese Unexamined Patent Application Publication No. 2012-210637.

The gas sensor 100 includes the sensor element 101, a protective cover 110 covering and protecting the front end side (lower end side in FIG. 1), which is one end side in the longitudinal direction, of the sensor element 101, an element sealing body 120 for sealing and fixing the sensor element 101, and a nut 130 attached to the element sealing body 120. As illustrated in FIG. 1, the gas sensor 100 is attached to, for example, a pipe 140, e.g., an exhaust pipe of a vehicle, and is used for measuring the concentration of specific gases, e.g., NOx and $O_2$, contained in an exhaust gas, which is a gas to be measured. In the present embodiment, the gas sensor 100 is specified to measure the NOx concentration as the specific gas concentration. The sensor element 101 includes a sensor element main body 101a and a porous protective layer 91 for covering the sensor element main body 101a. In this regard, the sensor element main body 101a refers to a portion other than the porous protective layer 91 in the sensor element 101.

The protective cover 110 includes a tubular inner protective cover 111, which has a bottom and which covers one end of the sensor element 101, and a tubular outer protective cover 112, which has a bottom and which covers the inner protective cover 111. A plurality of holes are formed in the inner protective cover 111 and the outer protective cover 112 so as to pass the gas to be measured through the protective cover 110. One end of the sensor element 101 is arranged in a space surrounded by the inner protective cover 111.

The element sealing body 120 includes a cylindrical main fitting 122, a ceramic supporter 124 sealed in an inner side through inner hole of the main fitting 122, and a compact 126 which is sealed in an inner side through hole of the main fitting 122 and which is produced by forming of a ceramic powder, e.g., talc. The sensor element 101 is located on the center axis of the element sealing body 120 and penetrates the element sealing body 120 in the front/rear direction. The compact 126 is compressed between the main fitting 122 and the sensor element 101. Consequently, the compact 126 seals the through hole in the main fitting 122 and, in addition, fixes the sensor element 101.

The nut 130 is fixed coaxially with the main fitting 122 and is provided with an external thread portion on the outer circumferential surface. The external thread portion of the nut 130 is inserted in a fitting member 141 welded to the pipe 140 and provided with an internal thread portion on the inner circumferential surface. Consequently, the gas sensor 100 can be fixed to the pipe 140 while one end of the sensor element 101 and the portion of the protective cover 110 are protruded into the pipe 140.

As illustrated in FIG. 3, the sensor element 101 is an element having a structure in which six layers composed of a first substrate layer 1, a second substrate layer 2, a third substrate layer 3, a first solid electrolyte layer 4, a spacer layer 5, and a second solid electrolyte layer 6, each being formed from an oxygen ion-conductive solid electrolyte layer of zirconia ($ZrO_2$) or the like, are stacked in that order from the bottom side in FIG. 3. Also, the solid electrolyte constituting these six layers is dense and airtight. The above-described sensor element 101 is produced by, for example, subjecting ceramic green sheets corresponding to the individual layers to predetermined processing, printing of circuit patterns, and the like, stacking them thereafter, and further performing firing so as to integrate the ceramic green sheets.

In one front end portion (frontward end portion) of the sensor element 101 and between the lower surface of the second solid electrolyte layer 6 and the upper surface of the first solid electrolyte layer 4, a gas inlet 10, a first diffusion-controlled portion 11, a buffer space 12, a second diffusion-controlled portion 13, a first internal space 20, a third diffusion-controlled portion 30, and a second internal space 40 are formed in that order so as to adjoin and communicate.

The gas inlet 10, the buffer space 12, the first internal space 20, and the second internal space 40 are spaces in the inside of the sensor element 101 by hollowing the spacer layer 5, where the upper portion is defined by the lower surface of the second solid electrolyte layer 6, the lower portion is defined by the upper surface of the first solid electrolyte layer 4, and the side portions are defined by the side surfaces of the spacer layer 5.

Each of the first diffusion-controlled portion 11, the second diffusion-controlled portion 13, and the third diffusion-controlled portion 30 is provided as two horizontally oriented (the longitudinal direction of the opening is a direction perpendicular to the drawing) slits. In this regard, the portions from the gas inlet 10 to the second internal space 40 may be referred to as a gas flow portion.

Meanwhile, at the position farther from the front end side than the gas flow portion, a reference gas introduction space 43 is provided at the location between the upper surface of the third substrate layer 3 and the lower surface of the spacer layer 5, where the side portions are defined by the side surfaces of the first solid electrolyte layer 4. For example, the air serving as the reference gas at the time of measurement of the NOx concentration is introduced into the reference gas introduction space 43.

An air introduction layer 48 is a layer composed of porous ceramics. The reference gas is introduced into the air introduction layer 48 through the gas introduction space 43. Also, the air introduction layer 48 is formed so as to cover a reference electrode 42.

The reference electrode 42 is an electrode formed so as to be sandwiched between the upper surface of the third substrate layer 3 and the first solid electrolyte layer 4 and, as described above, the air introduction layer 48 connected to the reference gas introduction space 43 is provided around the reference electrode 42. In addition, as described later, it is possible to measure the oxygen concentrations (oxygen partial pressures) in the first internal space 20 and the second internal space 40 by using the reference electrode 42.

In the gas flow portion, the gas inlet 10 is a part made open to the outside space, and the gas to be measured is taken from the outside space into the sensor element 101 through the gas inlet 10. The first diffusion-controlled portion 11 is a part for giving predetermined diffusion resistance to the gas to be measured, where the gas is taken from the gas inlet 10. The buffer space 12 is a space provided so as to lead the gas to be measured, where the gas is introduced from the first diffusion-controlled portion 11, to the second diffusion-controlled portion 13. The second diffusion-controlled portion 13 is a part for giving predetermined diffusion resistance to the gas to be measured, where the gas is introduced from the buffer space 12 to the first internal space 20. When the gas to be measured is introduced from the outside of the sensor element 101 into the first internal space 20, the gas to be measured, which is taken into the sensor element 101 through the gas inlet 10 rapidly because of the pressure fluctuation of the gas to be measured in the outside space (pulsation of an exhaust pressure in the case where the gas to be measured is an automotive exhaust gas), is not directly introduced into the first internal space 20 but introduced into the first internal space 20 after concentration variations of the gas to be measured are canceled through the first diffusion-controlled portion 11, the buffer space 12, and the second diffusion-controlled portion 13. Consequently, concentration variations of the gas to be measured, which is introduced into the first internal space 20, are made to be at an almost negligible level. The first internal space 20 is provided as a space for adjusting the oxygen partial pressure in the gas to be measured which is introduced through the second diffusion-controlled portion 13. The above-described oxygen partial pressure is adjusted by actuation of a main pump cell 21.

The main pump cell 21 is an electrochemical pump cell composed of an inside pump electrode 22 having a ceiling electrode portion 22a provided on an almost entire surface of the lower surface of the second solid electrolyte layer 6 facing the first internal space 20, an outside pump electrode 23 provided in a region, which corresponds to the ceiling electrode portion 22a, on the upper surface of the second solid electrolyte layer 6 so as to be exposed to the outside space, and the second solid electrolyte layer 6 sandwiched between these electrodes.

The inside pump electrode 22 is formed so as to extend over the upper and lower solid electrolyte layers (second solid electrolyte layer 6 and first solid electrolyte layer 4) defining the first internal space 20 and the spacer layer 5 providing the side walls. Specifically, the ceiling electrode portion 22a is formed on the lower surface of the second solid electrolyte layer 6 providing the ceiling surface of the first internal space 20 and a bottom electrode portion 22b is formed on the upper surface of the first solid electrolyte layer 4 providing the bottom surface. Then, side electrode portions (not shown in the drawing) are formed on the side wall surfaces (inner surfaces) of the spacer layer 5 constituting both side wall portions of the first internal space 20 so as to connect the ceiling electrode portion 22a to the bottom electrode portion 22b. Thus, the inside pump electrode 22 is disposed in the form of a tunnel-like structure in a zone where the side electrode portions are disposed.

The inside pump electrode 22 and the outside pump electrode 23 are formed as porous cermet electrodes (for example, a cermet electrode of Pt containing 1% of Au and $ZrO_2$). In this regard, the inside pump electrode 22 to contact with the gas to be measured is formed by using a material having weakened ability to reduce NOx components in the gas to be measured.

In the main pump cell 21, oxygen in the first internal space 20 can be pumped out to the outside space or oxygen in the outside space can be pumped into the first internal space 20 by applying a predetermined pump voltage Vp0 between the inside pump electrode 22 and the outside pump electrode 23 and passing a pump current Ip0 between the inside pump electrode 22 and the outside pump electrode 23 in the positive direction or negative direction.

In addition, in order to detect the oxygen concentration (oxygen partial pressure) in the atmosphere in the first internal space 20, an electrochemical sensor cell, that is, a main pump controlling oxygen partial pressure detection sensor cell 80 is constructed by the inside pump electrode 22, the second solid electrolyte layer 6, the spacer layer 5, the first solid electrolyte layer 4, the third substrate layer 3, and the reference electrode 42.

The oxygen concentration (oxygen partial pressure) in the first internal space 20 is determined by measuring the electromotive force V0 of the main pump controlling oxygen partial pressure detection sensor cell 80. Further, the pump current Ip0 is controlled by feedback-controlling the pump voltage Vp0 of a variable power supply 25 so as to make the electromotive force V0 constant. Consequently, the oxygen concentration in the first internal space 20 can be maintained at a predetermined constant value.

The third diffusion-controlled portion 30 is a part which gives predetermined diffusion resistance to the gas to be measured, the oxygen concentration (oxygen partial pressure) of the gas having been controlled by the operation of the main pump cell 21 in the first internal space 20, and leads the gas to be measured into the second internal space 40.

The second internal space 40 is provided as a space for performing a treatment related to the measurement of the nitrogen oxide (NOx) concentration in the gas to be measured that is introduced through the third diffusion-controlled portion 30. The NOx concentration is measured mainly in the second internal space 40 in which the oxygen concentration is adjusted by an auxiliary pump cell 50 and further the NOx concentration is measured by the operation of a measurement pump cell 41.

In the second internal space 40, the gas to be measured is further subjected to adjustment of the oxygen partial pressure by the auxiliary pump cell 50, the gas to be measured having been subjected to adjustment of the oxygen concentration (oxygen partial pressure) in the first internal space 20 in advance and, thereafter, having been introduced through the third diffusion-controlled portion 30. Consequently, the oxygen concentration in the second internal space 40 can be maintained constant with high accuracy and, therefore, the gas sensor 100 can measure the NOx concentration with high accuracy.

The auxiliary pump cell 50 is an auxiliary electrochemical pump cell constructed by an auxiliary pump electrode 51 having a ceiling electrode portion 51a provided on an almost entire surface of the lower surface of the second solid electrolyte layer 6 facing the second internal space 40, an outside pump electrode 23 (not limited to the outside pump electrode 23, and the sensor element 101 and an appropriate outside electrode will suffice), and the second solid electrolyte layer 6.

The above-described auxiliary pump electrode 51 is arranged in the second internal space 40 so as to have a similar tunnel-like structure to the above-described inside pump electrode 22 disposed in the first internal space 20. That is, a tunnel-like structure is constructed, in which the ceiling electrode portion 51a is formed on the second solid electrolyte layer 6 providing the ceiling surface of the second internal space 40, a bottom electrode portion 51b is formed on the first solid electrolyte layer 4 providing the bottom surface of the second internal space 40, and then, side electrode portions (not shown in the drawing) for connecting the ceiling electrode portion 51a to the bottom electrode portion 51b are formed on both side wall surfaces of the spacer layer 5 providing side walls of the second internal space 40. In this regard, the auxiliary pump electrode 51 is formed by using a material having weakened ability to reduce NOx components in the gas to be measured in the same manner as the inside pump electrode 22.

In the auxiliary pump cell 50, oxygen in the atmosphere in the second internal space 40 can be pumped out to the outside space or oxygen in the outside space can be pumped into the second internal space 40 by applying a predetermined pump voltage vp1 between the auxiliary pump electrode 51 and the outside pump electrode 23.

In addition, in order to control the oxygen partial pressure in the atmosphere in the second internal space 40, an electrochemical sensor cell, that is, an auxiliary pump controlling oxygen partial pressure detection sensor cell 81 is constructed by the auxiliary pump electrode 51, the reference electrode 42, the second solid electrolyte layer 6, the spacer layer 5, the first solid electrolyte layer 4, and the third substrate layer 3.

In this regard, the auxiliary pump cell 50 performs pumping by a variable power supply 52 which is voltage-controlled on the basis of the electromotive force V1 detected by the auxiliary pump controlling oxygen partial pressure detection sensor cell 81. Consequently, the oxygen partial pressure in the atmosphere in the second internal space 40 is controlled to a low partial pressure that does not substantially affect the measurement of NOx.

In addition to this, the pump current Ip1 thereof is used for controlling the electromotive force of the main pump controlling oxygen partial pressure detection sensor cell 80. Specifically, the pump current Ip1 serving as a control signal is input into the main pump controlling oxygen partial pressure detection sensor cell 80, and by controlling the electromotive force V0 thereof the gradient of the oxygen partial pressure in the gas to be measured, which is introduced from the third diffusion-controlled portion 30 into the second internal space 40, is controlled so as to be always constant. In the case of application as a NOx sensor, the oxygen concentration in the second internal space 40 is maintained at a constant value of about 0.001 ppm by the functions of the main pump cell 21 and the auxiliary pump cell 50.

The measurement pump cell 41 measures the NOx concentration in the gas to be measured in the second internal space 40. The measurement pump cell 41 is an electrochemical pump cell constructed by a measurement electrode 44 disposed on the upper surface of the first solid electrolyte layer 4 facing the second internal space 40 and at the position apart from the third diffusion-controlled portion 30, the outside pump electrode 23, the second solid electrolyte layer 6, the spacer layer 5, and the first solid electrolyte layer 4.

The measurement electrode 44 is a porous cermet electrode. The measurement electrode 44 also functions as a NOx reduction catalyst for reducing NOx present in the atmosphere in the second internal space 40. Further, the measurement electrode 44 is covered with a fourth diffusion-controlled portion 45.

The fourth diffusion-controlled portion 45 is a film composed of a ceramic porous body. The fourth diffusion-controlled portion 45 has a function of restricting the amount of NOx flowing into the measurement electrode 44 and, in addition, a function as a protective film for the measurement electrode 44. In the measurement pump cell 41, oxygen generated by decomposition of nitrogen oxides in the atmosphere around the measurement electrode 44 is pumped out and the amount of generation thereof can be detected as a pump current Ip2.

Also, in order to detect the oxygen partial pressure around the measurement electrode 44, an electrochemical sensor cell, that is, a measurement pump controlling oxygen partial pressure detection sensor cell 82 is constructed by the first solid electrolyte layer 4, the third substrate layer 3, the measurement electrode 44, and the reference electrode 42. A variable power supply 46 is controlled on the basis of the electromotive force V2 detected by the measurement pump controlling oxygen partial pressure detection sensor cell 82.

The gas to be measured, which is introduced into the second internal space 40, reaches the measurement electrode 44 through the fourth diffusion-controlled portion 45 under circumstances where the oxygen partial pressure is controlled. Nitrogen oxides in the gas to be measured around the measurement electrode 44 are reduced ($2NO \rightarrow N_2+O_2$) and oxygen is generated. Then, the resulting oxygen is pumped by the measurement pump cell 41. At that time, the voltage Vp2 of the variable power supply 46 is controlled so as to make the control voltage V2 detected by the measurement pump controlling oxygen partial pressure detection sensor cell 82 constant. The amount of oxygen generated around the measurement electrode 44 is proportional to the concentration of the nitrogen oxides in the gas to be measured and, therefore, the nitrogen oxide concentration in the gas to be measured is calculated by using the pump current Ip2 in the measurement pump cell 41.

In addition, in the case where the measurement electrode 44, the first solid electrolyte layer 4, the third substrate layer 3, and the reference electrode 42 are combined so as to constitute an oxygen partial pressure detection device as an electrochemical sensor cell, the electromotive force in accordance with the difference between the amount of oxygen generated by reduction of NOx components in the atmosphere around the measurement electrode 44 and the amount of oxygen contained in the reference air can be detected and, thereby, the concentration of NOx components in the gas to be measured can be determined.

Further, an electrochemical sensor cell 83 is constructed by the second solid electrolyte layer 6, the spacer layer 5, the first solid electrolyte layer 4, the third substrate layer 3, the outside pump electrode 23, and the reference electrode 42. The oxygen partial pressure in the gas to be measured in the outside of the sensor can be detected by the electromotive force Vref obtained by the sensor cell 83.

In the gas sensor 100 having the above-described configuration, the gas to be measured, which has an oxygen partial pressure always maintained at a low constant value (value that does not substantially affect the measurement of NOx) by actuation of the main pump cell 21 and the auxiliary pump cell 50, is fed to the measurement pump cell 41. Therefore, the NOx concentration in the gas to be measured can be determined on the basis of the pump current Ip2 that flows because oxygen, which is generated by reduction of NOx nearly in proportion to the NOx concentration in the gas to be measured, is pumped out of the measurement pump cell 41.

Further, in order to enhance the oxygen ion conductivity of the solid electrolyte, the sensor element 101 includes a heater portion 70 having a function of adjusting the temperature including heating the sensor element 101 and keeping the temperature. The heater portion 70 includes a heater connector electrode 71, a heater 72, a through hole 73, a heater insulating layer 74, and a pressure release hole 75.

The heater connector electrode 71 is an electrode formed so as to contact with the lower surface of the first substrate layer 1. The electric power can be supplied from the outside to the heater portion 70 by connecting the heater connector electrode 71 to an external power supply.

The heater 72 is an electric resistor formed to be sandwiched between the second substrate layer 2 and the third substrate layer 3 in the vertical direction. The heater 72 is connected to the heater connector electrode 71 through the through hole 73 and generates heat by being supplied with an electric power from the outside through the heater connector electrode 71 so as to heat the solid electrolyte constituting the sensor element 101 and keep the temperature.

Also, the heater 72 is embedded over an entire range from the first internal space 20 to the second internal space 40 and the entirety of the sensor element 101 can be adjusted to have a temperature at which the above-described solid electrolyte is activated.

The heater insulating layer 74 is an insulating layer formed on the upper and lower surfaces of the heater 72 by using an insulator, e.g., alumina. The heater insulating layer 74 is formed for the purpose of establishing electrical insulation between the second substrate layer 2 and the heater 72 and electrical insulation between the third substrate layer 3 and the heater 72.

The pressure release hole 75 is a part provided so as to penetrate the third substrate layer 3 and communicate with the reference gas introduction space 43 and is formed for the purpose of reducing an internal pressure increase associated with a temperature increase in the heater insulating layer 74.

Further, as illustrated in FIGS. 2 and 3, the sensor element main body 101a includes a coating layer 24. The coating layer 24 includes a coating layer 24a covering the upper surface side of the sensor element main body 101a (upper surface of the second solid electrolyte layer 6) and a coating layer 24b covering the lower surface side of the sensor element main body 101a (lower surface of the first substrate layer 1). In this regard, the coating layer 24a also covers the surface of the outside pump electrode 23. The coating layer 24 is composed of porous ceramics, e.g., alumina, zirconia, spinel, cordierite, or magnesia. In the present embodiment, the coating layer 24 is porous ceramic composed of alumina. The film thickness of the coating layer 24 is, for example, 5 to 50 µm and the porosity of the coating layer 24 is, for example, 10 percent by volume to 60 percent by volume, although not specifically limited. Also, the arithmetic average roughness Ra of the surface of the coating layer 24 (upper surface of the coating layer 24a and lower surface of the coating layer 24b) is preferably 2.0 to 5.0 µm. In this regard, the arithmetic average roughness Ra of the surface of the main body of the sensor element 101 (upper surface of the second solid electrolyte layer 6 and lower surface of the first substrate layer 1) to be provided with the coating layer 24 is, for example, 0.3 to 1.0 µm, although not specifically limited.

Also, as illustrated in FIGS. 2 and 3, part of the sensor element main body 101a is covered with a porous protective layer 91. The porous protective layer 91 includes porous protective layers 91a to 91e fanned on five surfaces, respectively, among the six surfaces of the sensor element main body 101a. The porous protective layer 91a covers part of the upper surface of the sensor element main body 101a (upper surface of the coating layer 24a). The porous protective layer 91b covers part of the lower surface of the sensor element main body 101a (lower surface of the coating layer 24b). The porous protective layer 91c covers part of the left surface of the sensor element main body 101a. The porous protective layer 91d covers part of the right surface of the sensor element main body 101a. The porous protective layer 91e covers the entirety of the front end surface of the sensor element main body 101a. In this regard, each of the porous protective layers 91a to 91d covers the entire region from the front end surface of the sensor element main body 101a to the rearward position at a distance L (refer to FIG. 3) on the surface, on which the porous protective layer is disposed, of the sensor element main body 101a. In addition, the porous protective layer 91a covers the portion provided with the outside pump electrode 23. The porous protective layer 91e also covers the gas inlet 10. However, the gas to be measured can pass through the porous protective layer 91e and reach the gas inlet because the porous protective layer 91e is a porous body. The porous protective layer 91 covers part of the sensor element main body 101a (portion from the front end surface to the position at the distance L, including the front end surface of the sensor element main body 101a) and protects that portion. The porous protective layer 91 has a function of, for example, suppressing occurrence of cracking in the sensor element main body 101a due to adhesion of moisture and the like in the gas to be measured. In addition, the porous protective layer 91a has functions of suppressing adhesion of oil components and the like contained in the gas to be measured to the outside pump electrode 23 and suppressing degradation of the outside pump electrode 23. In this regard, the distance L is specified to be within the range of (0<distance L<length in the longitudinal direction of the sensor element main body 101a) on the basis of the range of exposure of the sensor element main body 101a to the gas to be measured, the position of the outside pump electrode 23, and the like in the gas sensor 100.

The porous protective layer 91 is a porous body, preferably contains ceramic particles as constituent particles, and more preferably contains particles of at least one of alumina, zirconia, spinel, cordierite, titania, and magnesia. In the present embodiment, the porous protective layer 91 is composed of an alumina porous body. The porosity of the porous protective layer 91 is, for example, 5 percent by volume to 40 percent by volume. In addition, it is preferable that the material for the coating layers 24a and 24b is the same as the material for the porous protective layers 91a and 91b formed on the surface thereof because the adhesion is enhanced.

Figure 4:
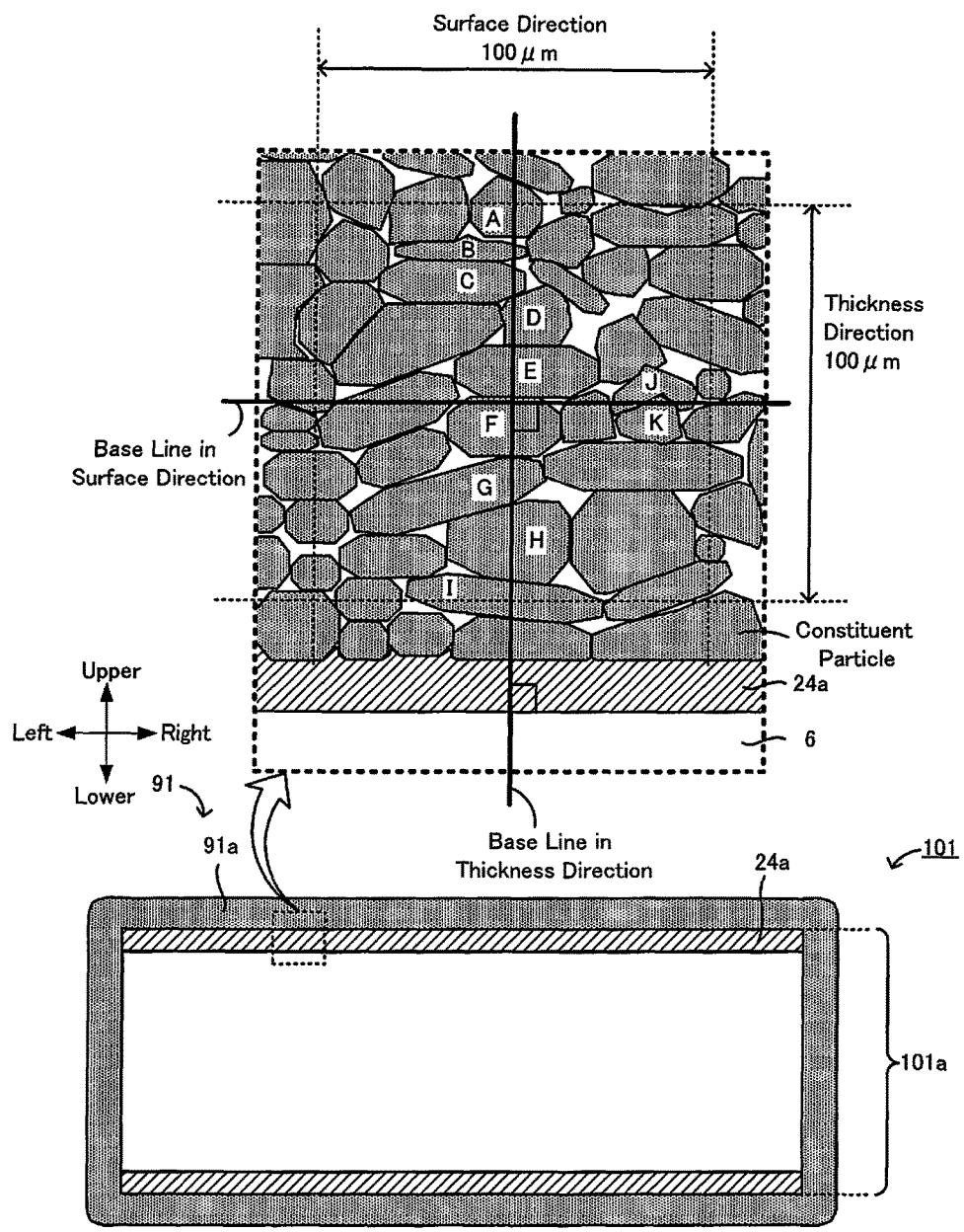

The porous protective layer 91 has the value of the number of interfaces in a unit thickness direction, which is the number of particle interfaces of constituent particles every 100 µm in the thickness direction, of 15 or more and 250 or less. The number of interfaces in a unit thickness direction will be described below. The number of interfaces in a unit thickness direction is measured by using an image (SEM image) obtained by observation of the porous protective layer 91 with a scanning electron microscope (SEM). FIG. 4 is a conceptual diagram illustrating the manner of measurement of the number of interfaces in a unit thickness direction and the like of the porous protective layer 91a. The upper part of FIG. 4 illustrates a conceptual diagram of the SEM image. The above-described image can be obtained as described below. Initially, the sensor element 101 is cut so that a cross-section along the right/left direction (width direction) of the sensor element 101 (refer to the lower part of FIG. 4) becomes an observation surface. Subsequently, the cut surface is embedded into a resin and is polished so as to prepare an observation sample. Then, the magnification of SEM is set at 3,000 times, and the observation surface of the observation sample is photographed, so that the SEM image as illustrated in the upper part of FIG. 4 is obtained.

Next, a base line in the thickness direction is drawn in the SEM image. The thickness direction is specified as a direction perpendicular to the surface of the solid electrolyte layer provided with the porous protective layer 91 in the SEM image. A straight line along the thickness direction is drawn as the base line in the thickness direction. In FIG. 4, the direction perpendicular to the upper surface of the second solid electrolyte layer 6 (vertical direction) is the thickness direction. In this regard, FIG. 4 illustrates an example of the SEM image including both the upper surface of the second solid electrolyte layer 6 and the porous protective layer 91a. However, it is only needed that the base line in the thickness direction can be drawn on the SEM image of the porous protective layer 91 (the thickness direction in the SEM image is determined). For example, the second solid electrolyte layer 6 and the porous protective layer 91a may be photographed as separate SEM images. Subsequently, in the SEM image, a region of 100 µm in the thickness direction is determined along the base line in the thickness direction, and particles intersecting the base line in the thickness direction in this region are specified among the constituent particles of the porous protective layer 91. In this regard, even in the case where the porous protective layer 91 contains a plurality of types of constituent particles, the types of the constituent particles are not specifically distinguished, and all particles intersecting the base line in the thickness direction are specified. Then, the number of interfaces between the specified particles is taken as the number of interfaces in a unit thickness direction. In FIG. 4, in the region of 100 µm in the thickness direction, nine particles A to I, among the constituent particles of the porous protective layer 91a, intersect the base line in the thickness direction. Consequently, in the example of FIG. 4, the value of the number of interfaces in a unit thickness direction of the porous protective layer 91a is 8, which is the number of interfaces between particles A to I (an interface between particles A and B, an interface between particles B and C, ..., an interface between particles H and I). In this regard, the case where particles in the SEM image are separated from each other, as particles A and B illustrated in FIG. 4, is counted as one interface between particles A and B. Therefore, the number of interfaces in a unit thickness direction is the value obtained by subtracting 1 from the number of particles intersecting the base line in the thickness direction in the region of 100 µm in the thickness direction (9 in FIG. 4). Meanwhile, in the case where the thickness of the porous protective layer 91a is less than 100 µm, the number of interfaces between constituent particles of the entire porous protective layer 91a in the thickness direction is measured along the base line in the thickness direction. Then, the measured value is converted to the value in the thickness of 100 µm, and the resulting value is taken as the number of interfaces in a unit thickness direction.

The number of interfaces in a unit thickness direction of each of the porous protective layers 91b to 91e can be derived in the same manner as that described above. In this regard, the thickness direction is determined on the basis of the SEM image of each of the porous protective layers 91b to 91e. For example, the thickness direction of the porous protective layer 91c is the right/left direction. Also, when measuring the number of interfaces in a unit thickness direction of the porous protective layer 91e, the cross-section along the front/rear direction (longitudinal direction) of the sensor element 101 is the observation surface.

In the present embodiment, each of the porous protective layers 91a to 91e (that is, the entirety of the porous protective layer 91) satisfies the above-described condition "the value of the number of interfaces in a unit thickness direction is 15 or more and 250 or less" (hereafter may be referred to as first condition). The value of the number of interfaces in a unit thickness direction of at least one of the porous protective layers 91a to 91e may be 17 or more, and the value is more preferably 30 or more. The value of the number of interfaces in a unit thickness direction of at least one of the porous protective layers 91a to 91e may be 200 or less, 150 or less, 100 or less, or 50 or less. Here, the thickness of the porous protective layer 91 is, for example, 1,000 µm or less, and may be 700 µm or less, 500 µm or less, 250 µm or less, 200 µm or less, or 150 µm or less. Also, the thickness of the porous protective layer 91 may be 50 µm or more, or 100 µm or more. Here, in the case where there is no irregularity in the distribution of the constituent particles in the thickness direction of the porous protective layer 91a, the total number of interfaces in the thickness direction can be derived on the basis of the total number of interfaces in thickness direction=the number of interfaces in unit thickness direction×thickness of porous protective layer 91a (µm)/100 µm, where the number of particle interfaces of constituent particles over the entirety of the thickness direction of the porous protective layer 91a is referred to as the total number of interfaces in the thickness direction. Also, the value of the total number of interfaces in the thickness direction of the porous protective layer 91a having a thickness of 50 µm or more and satisfying the first condition is 7.5 or more. The same goes for the porous protective layers 91b to 91e.

Meanwhile, the porous protective layer 91 has the value of the ratio of the number of interfaces (=the number of interfaces in a unit surface direction/the number of interfaces in a unit thickness direction) of the number of interfaces in a unit surface direction, which is the number of particle interfaces of constituent particles every 100 µm in the surface direction perpendicular to the thickness direction to the number of interfaces in a unit thickness direction of more than 0 and 0.7 or less. The number of interfaces in a unit surface direction is measured in the same manner as the number of interfaces in a unit thickness direction is measured. Initially, as illustrated in FIG. 4, a straight line perpendicular to the above-described base line in the thickness direction in the SEM image is drawn as a base line in the surface direction. Subsequently, in the SEM image, a region of 100 µm in the surface direction is determined along the base line in the surface direction. In this regard, the region of 100 µm in the surface direction is determined so that the base line in the thickness direction is positioned at the center in the surface direction (right/left direction in the drawing) of the region of 100 µm in the surface direction. Then, particles intersecting the base line in the surface direction in this region are specified among the constituent particles of the porous protective layer 91, and the number of interfaces between the specified particles is taken as the number of interfaces in a unit surface direction. The number of interfaces in a unit surface direction is the value obtained by subtracting 1 from the number of particles intersecting the base line in the surface direction in the region of 100 µm in the surface direction (6 in FIG. 4). In this regard, even in the case where a plurality of interfaces (2 in FIG. 4) intersecting the base line in the surface direction are present between two particles, as particles J and K in FIG. 4, the number of interfaces between the particles J and K is counted as one. This idea is the same when measuring the number of interfaces in a unit thickness direction.

In the present embodiment, each of the porous protective layers 91a to 91e (that is, the entirety of the porous protective layer 91) satisfies the above-described condition "the value of the ratio of the number of interfaces is more than 0 and 0.7 or less" (hereafter may be referred to as second condition). In this regard, the value of the ratio of the number of interfaces of at least one of the porous protective layers 91a to 91e may be 0.6 or less, and the value is preferably 0.4 or less, or 0.3 or less. The value of the ratio of the number of interfaces of at least one of the porous protective layers 91a to 91e may be 0.15 or more. The value of the ratio of the number of interfaces of at least one of the porous protective layers 91a to 91e may be 5 or more, the value may be 10.5 or less, or the value may be 10 or less. Here, in the case where the value of the ratio of the number of interfaces of the porous protective layer 91a is less than 1, as illustrated in FIG. 4, constituent particles of the porous protective layer 91a tend to have the shapes crashed in the thickness direction (shape in which the size in the thickness direction of the constituent particle is smaller than the size in the direction perpendicular to the thickness direction). The same goes for the porous protective layers 91b to 91e.

Next, the method for manufacturing the above-described gas sensor 100 will be described. In the method for manufacturing the gas sensor 100, initially, the sensor element main body 101a is produced. Thereafter, the sensor element 101 is produced by forming the porous protective layer 91 on the sensor element main body 101a.

To begin with, the method for manufacturing the sensor element main body 101a will be described. Initially, six unfired ceramic green sheets are prepared. Then, patterns of electrodes, insulating layers, resistance heating elements, and the like are printed on the individual ceramic green sheets in accordance with each of the first substrate layer 1, the second substrate layer 2, the third substrate layer 3, the first solid electrolyte layer 4, the spacer layer 5, and the second solid electrolyte layer 6. Meanwhile, a paste serving as the coating layer 24a after firing is screen-printed on the surface of the ceramic green sheet serving as the second solid electrolyte layer 6 (surface serving as the upper surface of the sensor element main body 101a). Likewise, a paste serving as the coating layer 24b after firing is screen-printed on the surface of the ceramic green sheet serving as the first substrate layer 1 (surface serving as the lower surface of the sensor element main body 101*a*). In this regard, a mixture of a raw material powder composed of the material for the above-described coating layer 24 (an alumina powder in the present embodiment), an organic binder, an organic solvent, and the like is used for the paste serving as the coating layers 24*a* and 24*b*. Also, preferably the paste is adjusted in advance so that the arithmetic average roughness Ra of the surface of the coating layer 24 after firing becomes 2.0 to 5.0 µm. For example, the arithmetic average roughness Ra of the surface of the coating layer 24 after firing can be made 2.0 to 5.0 µm by using a paste prepared by mixing a blend, in which the volume proportion of the raw material powder having a particle diameter D50=2 to 20 µm is 5 to 20 percent by volume, the binder solution is 20 to 40 percent by volume, a co-solvent is 30 to 50 percent by volume, and a dispersing agent is 1 to 5 percent by volume, for 2 to 6 hours at the number of revolutions of 50 to 250 rpm, although not specifically limited to this. After various patterns are formed, as described above, the green sheets are dried. Thereafter, they are stacked so as to form a laminate. The thus obtained laminate includes a plurality of sensor element main bodies 101*a*. The laminate is divided into the size of the sensor element main body 101*a* by cutting, and firing is performed at a predetermined firing temperature so as to obtain the sensor element main body 101*a*. In this regard, the method for producing the sensor element main body 101*a* by stacking a plurality of green sheets is known and is described in, for example, Japanese Unexamined Patent Application Publication No. 2008-164411 and Japanese Unexamined Patent Application Publication No. 2009-175099.

Figure 5:
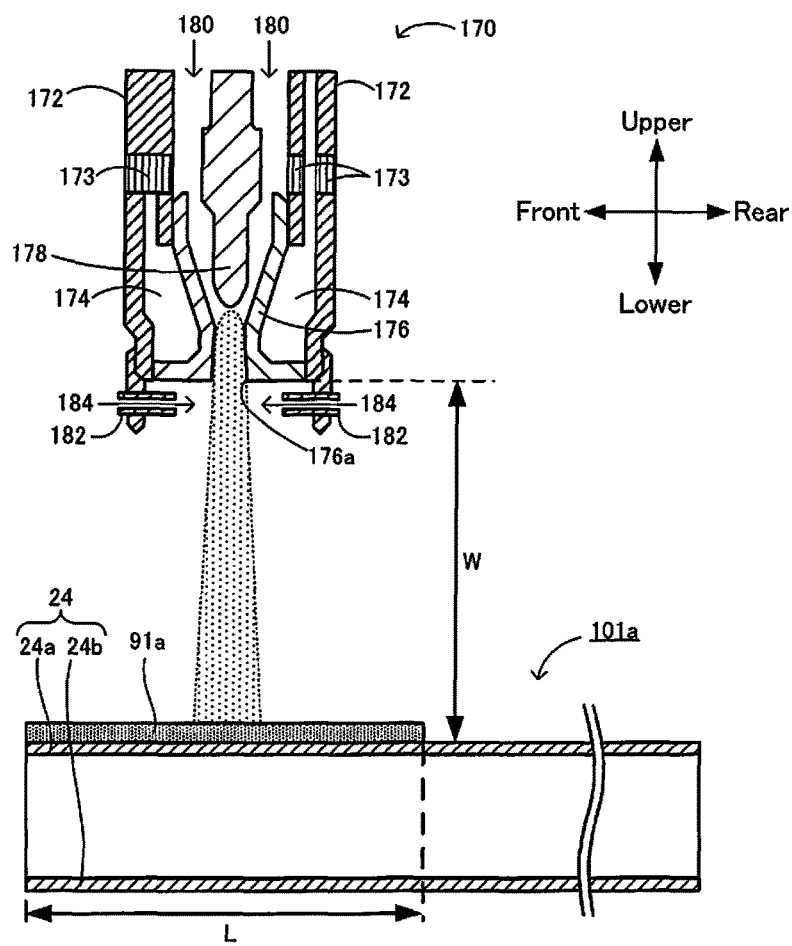
FIG. 5 is an explanatory diagram of plasma spraying with a plasma gun 170.

Next, the method for forming the porous protective layer 91 on the sensor element main body 101*a* will be described. In the present embodiment, the porous protective layers 91*a* to 91*e* are formed one by one by plasma spraying. FIG. 5 is an explanatory diagram of plasma spraying with a plasma gun 170. In this regard, FIG. 5 illustrates the state of formation of the porous protective layer 91*a* as an example and illustrates a cross-section of the plasma gun 170. The plasma gun 170 includes an anode 176 and a cathode 178 serving as electrodes for generating plasma and a substantially cylindrical peripheral portion 172 for covering them. The peripheral portion 172 includes an insulating portion (insulator) 173 so as to be insulated from the anode 176. A powder supply portion 182 for supplying a powder spray material 184 serving as the material for forming the porous protective layer 91 is formed at the lower end of the peripheral portion 172. A water cooling jacket 174 is disposed between the peripheral portion 172 and the anode 176 and, thereby, the anode 176 can be cooled. The anode 176 is formed into the shape of a tube and has a nozzle 176*a* opened downward. A plasma generation gas 180 is supplied between the anode 176 and the cathode 178 from above. In this regard, such a plasma gun 170 is known and is described in, for example, PTL 1 above.

When forming the porous protective layer 91*a*, a voltage is applied between the anode 176 and the cathode 178 of the plasma gun 170, and arc discharge is performed in the presence of the plasma generation gas 180 supplied so as to bring the plasma generation gas 180 into a high-temperature plasma state. The gas brought into the plasma state is ejected as a high-temperature high-speed plasma jet from the nozzle 176*a* downward in FIG. 5. On the other hand, the powder spray material 184 is supplied together with a carrier gas from the powder supply portion 182. Consequently, the powder spray material 184 is heat-melted and accelerated by plasma, collides with the surface (upper surface) of the sensor element main body 101*a*, and solidifies rapidly, so that the porous protective layer 91*a* is formed. In this regard, the direction of spraying of the plasma gun 170 (direction of the nozzle 176*a*) is not particularly limited insofar as the porous protective layer 91*a* can be formed. The porous protective layers 91*b* to 91*e* are formed one by one in the same manner except that the surfaces, on which the porous protective layers 91*a* to 91*b* are formed, of the sensor element main body 101*a* are different from each other. In this regard, the porous protective layers 91*a* and 91*b* are formed on the surfaces of the coating layers 24*a* and 24*b*, respectively, as described above. The porous protective layers 91*c* to 91*e* are formed directly on the surfaces of the solid electrolyte layer (each of layers 1 to 6) of the sensor element main body 101*a*. Here, plasma spraying is performed in, for example, an atmosphere of the air at ambient temperature. In the case where the porous protective layers 91*c* to 91*e* are formed one by one, preferably, the porous protective layers 91*a* and 91*b* to be formed on the coating layer 24 are formed in advance and the porous protective layers 91*c* to 91*e* are formed so that the end portions are connected to the porous protective layers which have been formed. Also, at least two of the porous protective layers 91*a* to 91*e* may be formed at the same time. In this manner, the porous protective layers 91*a* to 91*e* are formed on the upper, lower, left, and right surfaces and the front end surface, respectively, of the sensor element main body 101*a* so as to constitute the porous protective layer 91 and obtain the sensor element 101.

Here, as for the plasma generation gas 180, for example, an inert gas, e.g., an argon gas, can be used. Also, a mixture of argon and hydrogen is preferably used as the plasma generation gas 180 because plasma is generated easily. A mixture of argon and nitrogen may be used as the plasma generation gas 180. The flow rate of the argon gas is, for example, 40 to 50 L/min, the supply pressure is, for example, 0.5 to 0.6 MPa, the flow rate of hydrogen is, for example, 9 to 11 L/min, and the supply pressure is, for example, 0.5 to 0.6 MPa, although not specifically limited. The voltage applied between the anode 176 and the cathode 178 is, for example, a direct current voltage of 50 to 70 V, and the current is, for example, 500 to 550 A. In this regard, the number of interfaces in a unit thickness direction and the ratio of the number of interfaces of the porous protective layer 91 can be adjusted by adjusting the plasma generation condition (the flow rate and the supply pressure of the plasma generation gas 180, the applied voltage, and the current). Preferably, the plasma generation condition is adjusted so that constituent particles of the porous protective layer 91 have the shapes crashed in the thickness direction (refer to FIG. 4). In the case where the constituent particles have the shapes crashed in the thickness direction, the number of interfaces in a unit thickness direction increases easily and, therefore, the value of the number of interfaces in a unit thickness direction can be made 15 or more relatively easily. Also, in the case where the constituent particles have the shapes crashed in the thickness direction, the ratio of the number of interfaces decreases easily and, therefore, the value of the ratio of the number of interfaces can be made more than 0 and 0.7 or less relatively easily. For example, the powder spray material 184 is melted easily by setting the applied voltage and the current at relatively high values, as described above, and the constituent particles have the shapes crashed in the thickness direction easily when the constituent particles collide with the surface of the sensor element main body 101*a*. Likewise, it is preferable that the flow rate and the supply pressure of the plasma generation gas 180 be set at relatively high values, as described above.

The powder spray material 184 is a powder serving as the material for the above-described porous protective layer 91 and is an alumina powder in the present embodiment. The particle diameter of the powder spray material 184 is, for example, 1 µm to 50 µm, and more preferably 1 µm to 20 µm, although not specifically limited. As for the carrier gas used for supply of the powder spray material 184, for example, the same argon gas as the plasma generation gas 180 can be used. The flow rate of the carrier gas is, for example, 3 to 4 L/min and the supply pressure is, for example, 0.5 to 0.6 MPa, although not specifically limited. In this regard, the number of interfaces in a unit thickness direction and the number of interfaces in a unit surface direction of the porous protective layer 91 can be adjusted by adjusting the particle diameter of the powder spray material 184. As the particle diameter decreases, the number of interfaces in a unit thickness direction and the number of interfaces in a unit surface direction increase easily. However, if the particle diameter is too small, the powder supply portion 182 is plugged easily. Therefore, it is preferable that the sphericity of the particle of the powder spray material 184 be increased or the supply pressure of the carrier gas be increased.

When performing plasma spraying, the distance W between the nozzle 176a that is a plasma gas outlet in the plasma gun 170 and the surface to be provided with the porous protective layer 91 of the sensor element main body 101a (upper surface of the coating layer 24a in FIG. 5) is preferably 50 mm to 300 mm. The distance W may be 120 mm to 250 mm. Also, plasma spraying may be performed while the plasma gun 170 is moved (movement in the right/left direction in FIG. 5) appropriately in accordance with the area of the porous protective layer 91 to be formed. At that time as well, the distance W is preferably maintained within the above-described range. The duration of the plasma spraying may be determined appropriately in accordance with the film thickness and the area of the porous protective layer 91 to be formed. In this regard, in the case where the porous protective layer 91 is formed on part of the surface of the sensor element main body 101a (region from the front end to the rearward position at a distance L), as in the case where the porous protective layer 91a to porous protective layer 91d are formed, the region to be provided with no porous protective layer 91 may be covered with a mask.

After the sensor element 101 is obtained, the sensor element 101 is made to penetrate through the supporter 124 and the compact 126 prepared, these are inserted into the through hole inside the main fitting 122 from the upper side in FIG. 1, and the sensor element 101 is fixed with the element sealing body 120. Then, the nut 130, the protective cover 110, and the like are attached, so that the gas sensor 100 is obtained. In this regard, such a method for manufacturing the gas sensor is known and is described in, for example, International Publication No. 2013/005491.

When the thus configured gas sensor 100 is used, the gas to be measured in the pipe 140 flows into the cover 110, reaches the sensor element 101, passes through the porous protective layer 91, and flows into the gas inlet 10. Subsequently, the sensor element 101 detects the NOx concentration in the gas to be measured, which flows into the gas inlet 10. At this time, moisture contained in the gas to be measured may enter the protective cover 110 and adhere to the surface of the porous protective layer 91. As described above, the sensor element main body 101a is adjusted to the temperature (for example, 800° C.), at which the solid electrolyte is activated, by the heater 72. If moisture adheres to the sensor element 101, the temperature is lowered sharply, and cracking may occur in the sensor element main body 101a. Here, the porous protective layer 91 according to the present invention has the value of the number of interfaces in a unit thickness direction of 15 or more. As the number of interfaces in a unit thickness direction increases, occurrence of heat conduction in the thickness direction of the porous protective layer 91 tends to become difficult. That is, cooling of the sensor element main body 101a in the case where moisture adheres to the surface of the porous protective layer 91 tends to be suppressed. The reason for this is considered to be that the heat conduction between the constituent particles does not occur easily as compared with the heat conduction in the constituent particle. Then, the value of the number of interfaces in a unit thickness direction is 15 or more and, thereby, an effect of suppressing cooling of the sensor element main body 101a, that is, an effect of improving the waterproofing performance of the sensor element 101, is obtained and occurrence of cracking is suppressed. In this regard, as the value of the number of interfaces in a unit thickness direction increases, the number of constituent particles per unit thickness in the porous protective layer 91 increases and the gas to be measured does not easily pass through the porous protective layer 91 to reach the sensor element main body 101a. If the value of the number of interfaces in a unit thickness direction is 250 or less, the gas to be measured can pass through the porous protective layer 91. Also, in the case where the value of the number of interfaces in a unit thickness direction of the porous protective layer 91 is 100 or less, or 50 or less, the gas to be measured passes through the porous protective layer 91 more easily, so that degradation in the responsiveness of the sensor element 101 can be suppressed.

Also, as the ratio of the number of interfaces decreases, heat conduction in the surface direction (direction perpendicular to the thickness direction) of the porous protective layer 91 tends to occur as compared with heat conduction in the thickness direction of the porous protective layer 91. The reason for this is considered to be that the heat conduction between the constituent particles does not occur easily as compared with the heat conduction in the constituent particle. Consequently, as the ratio of the number of interfaces decreases, cooling of only part of the sensor element main body 101a in the case where moisture adheres to the surface of the porous protective layer 91 tends to be suppressed. Then, the ratio of the number of interfaces is 0.7 or less and, thereby, an effect of suppressing occurrence of cracking due to rapid cooling of only part (portion to which moisture adheres) of the sensor element main body 101a, that is, an effect of improving the waterproofing performance of the sensor element 101, is obtained.

Here, the correspondence between the constituent elements of the present embodiment and the constituent elements of the present invention will be made clear. The sensor element 101 of the present embodiment corresponds to the gas sensor element of the present invention, the sensor element main body 101a corresponds to the element main body, and the porous protective layer 91 corresponds to the protective layer. Also, the element sealing body 120 corresponds to the fixing member.

According to the above-described gas sensor 100 of the present embodiment, the sensor element 101 includes the sensor element main body 101a including an oxygen ion-conductive solid electrolyte layer (each of layers 1 to 6) and the porous protective layer 91 covering at least part of the sensor element main body 101*a*. Then, the porous protective layer 91 has the value of the number of interfaces in a unit thickness direction of 15 or more, so that the waterproofing performance of the sensor element 101 can be improved. Also, the porous protective layer 91 has the value of the number of interfaces in a unit thickness direction of 250 or less, so that the gas can pass through the porous protective layer 91.

Also, the porous protective layer 91 has the value of the ratio of the number of interfaces (=the number of interfaces in a unit surface direction/the number of interfaces in a unit thickness direction) of more than 0 and 0.7 or less, so that the waterproofing performance of the sensor element 101 can be improved.

Also, the waterproofing performance of the sensor element 101 can be further improved by specifying the value of the number of interfaces in a unit thickness direction of the porous protective layer 91 to be 30 or more. In addition, even in the case where the thickness of the porous protective layer 91 is 500 μm or less, an effect of improving the waterproofing performance of the sensor element 101 can be obtained. Here, in the case where the thickness of the porous protective layer 91 is a relatively low 500 μm or less, the waterproofing performance of the sensor element 101 becomes insufficient easily. The waterproofing performance of the sensor element 101 is improved by the porous protective layer 91 satisfying at least one of the first condition and the second condition. Therefore, application of the present invention to such a relatively thin porous protective layer 91 has great significance.

Further, the porous protective layer 91 contains ceramic particles as constituent particles. The ceramic particles are suitable for a protective layer of the sensor element 101 from the viewpoint of at least one of strength, heat resistance, and corrosion resistance. Also, the porous protective layer 91 contains particles of at least one of alumina, zirconia, spinel, cordierite, titania, and magnesia as the constituent particles. These materials have high heat resistance and, therefore, are suitable for the protective layer of the sensor element 101.

In addition, the sensor element main body 101*a* has long lengths of rectangular parallelepiped shape, and the porous protective layer 91 covers one end surface (front end surface) in the longitudinal direction of the sensor element main body 101*a* and regions from the edges on the one end surface sides of four surfaces (upper, lower, left, and right surfaces) perpendicular to the one end surface to the position at a distance L in the longitudinal direction of the sensor element main body 101*a* (where 0<distance L<length in the longitudinal direction) of the sensor element main body 101*a*. In the case where the porous protective layer 91 covers five surfaces as described above, an effect of protecting the sensor element main body 101*a* by the porous protective layer 91 is enhanced as compared with the case where, for example, the porous protective layer 91 covers only four surfaces at most.

Note that, needless to say, the present invention is not limited to the above-described embodiments and can be executed in various forms within the technical scope of the present invention.

For example, in the above-described embodiment, the porous protective layer 91 satisfies both the first condition and the second condition, although it is only needed to satisfy any one of the conditions.

In the above-described embodiment, all the porous protective layers 91*a* to 91*e* satisfy the first condition, although it is only needed that at least one of the porous protective layers 91*a* to 91*e* satisfies the first condition. In the case where at least one of the porous protective layers 91*a* to 91*e* satisfies the first condition, at least the porous protective layer satisfying the first condition exhibits the above-described effects. Therefore, for example, the value of the number of interfaces in a unit thickness direction of any one of the porous protective layers 91*a* to 91*e* may be less than 15 or more than 250. However, it is preferable that the number of porous protective layers satisfying the first condition, among the porous protective layers 91*a* to 91*e*, be large and it is more preferable that each of the porous protective layers 91*a* to 91*e* (that is, the entirety of the porous protective layer 91) satisfies the first condition. Likewise, in the case where at least one of the porous protective layers 91*a* to 91*e* satisfies the second condition, at least the porous protective layer satisfying the second condition exhibits the above-described effects.

The above-described embodiment makes no reference to the place, at which the number of interfaces in a unit thickness direction is measured, of the porous protective layer 91*a*, for example. This will be described below. In this regard, the same explanation goes for the porous protective layers 91*b* to 91*e*. If any one place of the porous protective layer 91*a* satisfies the first condition, the above-described effects are exhibited as compared with the case where no place satisfies the first condition. However, it is preferable that the first condition be satisfied at a plurality of places in different surface directions. For example, it is preferable that an average value of the number of interfaces in a unit thickness direction be 15 or more and 250 or less, where measurement is performed at arbitrary five places, which are at a distance from each other, in the surface direction of the porous protective layer 91*a*. Likewise, as for the ratio of the number of interfaces, if any one place of the porous protective layer 91*a* satisfies the second condition, the above-described effects are exhibited as compared with the case where no place satisfies the second condition. However, it is preferable that the second condition be satisfied at a plurality of places in different surface directions. For example, it is preferable that an average value of the ratio of the number of interfaces be more than 0 and 0.7 or less, where measurement is performed at arbitrary five places, which are at a distance from each other, in the surface direction of the porous protective layer 91*a*. Meanwhile, in the case where the porous protective layer 91*a* has a plurality of portions in which the statuses of constituent particles (for example, material, proportion, average particle diameter, and the like of constituent particles) are different, it is only needed that at least one portion satisfies at least one of the first condition and the second condition. For example, in the case where the porous protective layer 91*a* includes a plurality of layers in the thickness direction, it is only needed that at least one layer satisfies at least one of the first condition and the second condition. The same goes for the case where the porous protective layer 91*a* has a plurality of portions in which the statuses of constituent particles are different in the surface direction (forward, backward, left, and right directions).

In the above-described embodiment, the porous protective layer 91 includes the porous protective layers 91*a* to 91*e*, although not limited to this. The porous protective layer 91 is only needed to cover at least part of the sensor element main body 101*a*. For example, the porous protective layer 91 does not necessarily include at least one of the porous protective layers 91*a* to 91*e*. Meanwhile, the porous protective layer 91 is a porous body, although not limited to this.

In the above-described embodiment, the porous protective layer 91 is formed by plasma spraying, although not limited to this. For example, the porous protective layer 91 may be formed by another spraying, e.g., high-speed flame spraying, arc spraying, or laser spraying. Alternatively, the porous protective layer 91 may be formed by forming a coating film from a slurry on the surface of the sensor element main body 101*a* by not only spraying but also another production method (for example, screen printing, dipping, and a gel casting method) and firing the coating film. Such a slurry can be formed by, for example, dispersing a raw material powder (ceramic particles or the like) of the porous protective layer 91 into a solvent. Also, it is preferable that at least one of a sintering aid (binder) and a pore-forming material be added to the slurry. In the case where the gel casting method is used, an organic solvent, a dispersing agent, and a gelling agent (for example, isocyanates and polyols) are further added to the slurry. In this regard, in the case where the porous protective layer 91 is formed by firing the coating film, firing of the coating film and firing of the sensor element main body 101*a* may be performed at the same time.

In the above-described embodiment, the constituent particles of the porous protective layer 91 tend to have the crashed shapes, as illustrated in FIG. 4, although not limited to this. Even when the constituent particles are not crashed, the above-described effects thereof are obtained insofar as the value of the number of interfaces in a unit thickness direction is 15 or more. Also, in the above-described embodiment, the plasma generation condition is adjusted so as to crash the constituent particles of the porous protective layer 91, although not limited to this. For example, raw material particles serving as the constituent particles of the porous protective layer 91 may be subjected to shearing, crashing, polishing, or the like with a roll or the like so as to make the cross-sections of particles elliptical in advance. In this regard, for example, in the case where the porous protective layer 91 is formed by screen printing, it is possible that the constituent particles of the porous protective layer 91 tend to have the shapes crashed in the thickness direction by making the raw material particles elliptical because the direction of the major axis of the ellipse of the raw material particle tends to become the direction along the surface direction easily due to shear stress of a squeegee pressure. In the case where the porous protective layer 91 is formed by dipping, the direction of the major axis of the ellipse of the raw material particles tends to become the direction along the surface direction easily due to shear stress on the basis of dragging (pulling up of the sensor element main body 101*a* from the slurry) and the surface tension of the slurry by making the raw material particles elliptical. In this regard, when forming the porous protective layers 91*a* to 91*d* by dipping, it is preferable that the sensor element main body 101*a* be pulled up from the slurry along the front/rear direction (longitudinal direction of the sensor element main body 101*a*). When forming the porous protective layer 91*e* by dipping, it is preferable that the sensor element main body 101*a* be pulled up from the slurry along the vertical direction or right/left direction (direction perpendicular to the longitudinal direction of the sensor element main body 101*a*). Meanwhile, in the case where the porous protective layer 91 is formed by the gel casting method, the constituent particles of the porous protective layer 91 tend to have the shapes crashed in the thickness direction by, for example, pressing the slurry in the thickness direction before the slurry covering the sensor element main body 101*a* is solidified.

In the above-described embodiment, the sensor element main body 101*a* includes the coating layers 24*a* and 24*b*, although not limited to this. The coating layer 24 is only needed to be formed in part of the region, which is covered by the porous protective layer 91, of the surface of the sensor element main body 101*a*. For example, one of the coating layers 24*a* and 24*b* is not necessarily provided. A coating layer covering the surface other than the upper and lower surfaces of the sensor element main body 101*a* may be further provided. Also, the sensor element main body 101*a* does not necessarily include the coating layer.

EXAMPLES

Specific production example of the sensor elements will be described below as examples. Experimental examples 3 to 11, 16 to 19 and 22 to 25 correspond to the examples of the first gas sensor element according to the present invention, Experimental examples 3 to 9, 12 to 13, 16 to 19 and 22 to 25 correspond to the examples of the second gas sensor element according to the present invention, and Experimental examples 1, 2, 14, 15, 20, and 21 correspond to the comparative examples. In this regard, the present invention is not limited to the examples below.

Experimental Example 1

In Experimental example 1, the sensor element 101 illustrated in FIGS. 2 and 3 was formed following the method for manufacturing the sensor element 101 of the above-described embodiment. Specifically, to begin with, the sensor element main body 101*a* having a length of 67.5 mm in the front/rear direction, a width of 4.25 mm in the right/left direction, and a thickness of 1.45 mm in the vertical direction was produced. In this regard, when producing the sensor element main body 101*a*, ceramic green sheets were prepared by mixing zirconia particles containing 4 percent by mole of yttria and serving as a stabilizer, an organic binder, and an organic solvent and performing tape forming. Further, a paste for forming the coating layer 24 was prepared as described below. The paste was prepared by blending a raw material powder (alumina powder) having a particle diameter of D50=5 μm in a volume proportion of 10 percent by volume, 40 percent by volume of binder solution (polyvinylacetal and butyl carbitol), 45 percent by volume of co-solvent (acetone), and 5 percent by volume of dispersing agent (polyoxyethylene styrenated phenyl ether) and performing mixing for 3 hours at the number of revolutions of pot mill mixer of 200 rpm.

Subsequently, the porous protective layer 91 was produced by forming the porous protective layers 91*a*, 91*b*, 91*c*, 91*d*, and 91*e* in that order on the surface of the sensor element main body 101*a*, so that the sensor element 101 of Experimental example 1 was produced. The plasma spraying condition for forming the porous protective layer 91 was as described below. A mixture of an argon gas (flow rate 50 L/min, supply pressure 0.5 MPa) and hydrogen (flow rate 10 L/min, supply pressure 0.5 MPa) was used as the plasma generation gas 180. The voltage applied between the anode 176 and the cathode 178 was a direct current voltage of 70 V. The current was 500 A. An alumina powder having an average particle diameter of 30 μm was used as the powder spray material 184. The carrier gas used for supplying the powder spray material 184 was an argon gas (flow rate 4 L/min, supply pressure 0.5 MPa). The distance W was 150 mm. The distance L was 10 mm. Here, plasma spraying was performed in an air atmosphere at ambient temperature. The direction of spraying of the plasma gun 170 (direction of the nozzle 176*a*) was perpendicular to the surface to be provided with the porous protective layer 91 in the sensor element 101. The thickness measured with a micrometer of each of the porous protective layers 91*a* to 91*e* was 100 μm. Also, the value of the number of interfaces in a unit thickness direction measured by the above-described method of each of the porous protective layers 91a to 91e was 10. The value of the number of interfaces in a unit surface direction measured by the above-described method of each of the porous protective layers 91a to 91e was 13. The value of the ratio of the number of interfaces of each of the porous protective layers 91a to 91e was 1.30.

Experimental Examples 2 to 9

In Experimental examples 2 to 9, the sensor element 101 was produced in the same manner as Experimental example 1 except that the plasma spraying condition (average particle diameter of the powder spray material 184, distance W, applied voltage, and current) was variously changed as shown in Table 1. In each of Experimental examples 2 to 9, the thickness of each of the porous protective layers 91a to 91e was 100 μm.

[Evaluation of Waterproofing Performance]

The performance of the porous protective layer 91 (waterproofing performance of the sensor element 101) of the sensor element of each of Experimental examples 1 to 9 was evaluated. Specifically, initially, the heater 72 was energized, the temperature was set at 800° C., and the sensor element 101 was heated. In this state, the main pump cell 21, the auxiliary pump cell 50, the main pump controlling oxygen partial pressure detection sensor cell 80, the auxiliary pump controlling oxygen partial pressure detection sensor cell 81, and the like were actuated in an air atmosphere and the oxygen concentration in the first internal space 20 was controlled so as to be maintained at a predetermined constant value. Then, after waiting stabilization of the pump current Ip0, water was dropped on the porous protective layer 91, and presence or absence of a crack in the sensor element 101 was determined on the basis of whether the pump current Ip0 changed to a value exceeding a predetermined threshold value or not. In this regard, if cracking occurs in the sensor element 101 because of thermal shock due to a water droplet, oxygen passes through the cracked portion and flows into the first internal space 20 easily, so that the value of the pump current Ip0 increases. Therefore, in the case where the pump current Ip0 exceeded the predetermined threshold value determined on the basis of an experiment, it was judged that cracking occurred in the sensor element 101 because of the water droplet. Also, the amount of the water droplet was increased up to 30 μL gradually, a plurality of tests were performed, and the maximum amount of the water droplet, at which cracking did not occur, was taken as the amount of waterproofing performance. Then, five sensor elements 101 of each of Experimental examples 1 to 9 were prepared, and the average value of the five amounts of waterproofing performance of each of Experimental examples 1 to 9 was derived. The waterproofing performance of the sensor element 101 of each of Experimental examples 1 to 9 was evaluated, where the average value of the amount of waterproofing performance of less than 10 μL was specified to be poor, 10 μL or more was specified to be good, and 30 μL (no crack was generated) was specified to be very good.

Table 1 collectively shows the plasma spraying condition (average particle diameter of the powder spray material 184, distance W, applied voltage, and current), measurement results (the number of interfaces in a unit thickness direction, the number of interfaces in a unit surface direction, and the ratio of the number of interfaces), and evaluation results (average value of the amount of waterproofing performance and evaluation of the waterproofing performance) of each of Experimental examples 1 to 9. In this regard, the symbol X indicates poor, the symbol ○ indicates good, and the symbol ⊙ indicates very good. Here, in the same manner as in Experimental example 1, the number of interfaces in a unit thickness direction of each of the porous protective layers 91a to 91e in Experimental example 2 was the same value, and the number of interfaces in a unit surface direction of each of the porous protective layers 91a to 91e in Experimental example 2 was the same value. The same went for Experimental examples 3 to 9.

TABLE 1

|  |  | Experimental Example 1 | Experimental Example 2 | Experimental Example 3 | Experimental Example 4 | Experimental Example 5 | Experimental Example 6 | Experimental Example 7 | Experimental Example 8 | Experimental Example 9 |
|---|---|---|---|---|---|---|---|---|---|---|
| Spraying Condition | Average Particle Diameter of Powder Spray Material (μm) | 30 | 30 | 20 | 20 | 20 | 20 | 10 | 10 | 10 |
|  | Distance W (mm) | 150 | 200 | 150 | 200 | 150 | 200 | 150 | 200 | 150 |
|  | Applied Voltage (V) | 70 | 70 | 70 | 70 | 80 | 80 | 70 | 70 | 80 |
|  | Current (A) | 500 | 500 | 500 | 500 | 600 | 600 | 500 | 500 | 600 |
| Measurement Result | Number of Interfaces in Unit Thickness Direction | 10 | 14 | 17 | 19 | 22 | 30 | 35 | 37 | 45 |
|  | Number of Interfaces in Unit Surface Direction | 13 | 11 | 10 | 9 | 10 | 8 | 8 | 7 | 7 |
|  | Ratio of Number of Interfaces | 1.30 | 0.79 | 0.59 | 0.47 | 0.45 | 0.27 | 0.23 | 0.19 | 0.16 |
| Evaluation Result | Average Value of Amount of Waterproofing (μL) | 6.2 | 8.2 | 11.2 | 14.2 | 13.7 | 30 | 30 | 30 | 30 |
|  | Evaluation of Waterproofing Performance | X | X | ○ | ○ | ○ | ⊙ | ⊙ | ⊙ | ⊙ |

As is clear from Table 1, it was ascertained from the results of Experimental examples 1 to 9 that in the case where the value of the number of interfaces in a unit thickness direction of the porous protective layer 91 was 15 or more, or 17 or more, occurrence of cracking was suppressed and the waterproofing performance was improved. Also, it was ascertained that in the case where the value of the number of interfaces in a unit thickness direction of the porous protective layer 91 was 30 or more, the waterproofing performance was further improved.

Also, it was ascertained that in the case where the ratio of the number of interfaces of the porous protective layer 91 was 0.7 or less, or 0.6 or less, occurrence of cracking was suppressed and the waterproofing performance was improved. In addition, it was ascertained that in the case where the ratio of the number of interfaces of the porous protective layer 91 was 0.4 or less, or 0.3 or less, the waterproofing performance was further improved.

Experimental Examples 10 to 13

In Experimental examples 10 to 13, the sensor element 101 was produced in the same manner as Experimental example 1 except that the plasma spraying condition was variously changed as shown in Table 2. In each of Experimental examples 10 to 13, the thickness of each of the porous protective layers 91a to 91e was 100 μm. The waterproofing performance of each of Experimental examples 10 to 13 was evaluated in the same manner as Experimental examples 1 to 9. Table 2 collectively shows the plasma spraying condition, measurement results, and evaluation results of each of Experimental examples 10 to 13. It was ascertained from the results of Experimental examples 10 and 11 that in the case where the porous protective layer 91 satisfied the first condition, even when the second condition was not satisfied, the waterproofing performance was improved as compared with the cases of Experimental examples 1 and 2 in which neither the first condition nor the second condition was satisfied. Also, it was ascertained from the results of Experimental examples 12 and 13 that in the case where the porous protective layer 91 satisfied the second condition, even when the first condition was not satisfied, the waterproofing performance was improved as compared with the cases of Experimental examples 1 and 2 in which neither the first condition nor the second condition was satisfied.

TABLE 2

|  |  | Experimental Example 10 | Experimental Example 11 | Experimental Example 12 | Experimental Example 13 |
| --- | --- | --- | --- | --- | --- |
| Spraying Condition | Average Particle Diameter of Powder Spray Material (μm) | 20 | 30 | 20 | 20 |
|  | Distance W (mm) | 200 | 225 | 130 | 130 |
|  | Applied Voltage (V) | 60 | 80 | 70 | 60 |
|  | Current (A) | 450 | 600 | 500 | 450 |
| Measurement Result | Number of Interfaces in Unit Thickness Direction | 18 | 17 | 14 | 12 |
|  | Number of Interfaces in Unit Surface Direction | 13 | 15 | 9 | 8 |
|  | Ratio of Number of Interfaces | 0.72 | 0.88 | 0.64 | 0.67 |
| Evaluation Result | Average Value of Amount of Waterproofing (μL) | 11.5 | 10.3 | 11.8 | 11.2 |
|  | Evaluation of Waterproofing Performance | ◯ | ◯ | ◯ | ◯ |

Experimental Examples 14 to 19

In Experimental examples 14 to 19, the sensor element 101 was produced in the same manner as Experimental examples 1 to 4, 7, and 9 except that the thickness of each of the porous protective layers 91a to 91e was 50 μm. The waterproofing performance of each of Experimental examples 14 to 19 was evaluated in the same manner as Experimental examples 1 to 9. Table 3 collectively shows the plasma spraying condition, measurement results, and evaluation results of each of Experimental examples 14 to 19. In this regard, the value of the number of interfaces in a unit thickness direction in each of Experimental examples 14 to 19 was a value converted from a measurement value (value is twice the measurement value), where the number of interfaces between constituent particles was measured in a region of 50 μm in the thickness direction along the reference line in the thickness direction. In Experimental examples 16 to 19, even when the thickness of the porous protective layer 91 was 50 μm, the evaluation of the waterproofing performance was good. Therefore, it was able to be ascertained that the effects of the present invention were obtained. Also, in Experimental examples 16 to 19, it was able to be ascertained that the waterproofing performance was improved as compared with Experimental examples 1 and 2 in which the thickness was 100 μm.

TABLE 3

|  |  | Experimental Example 14 | Experimental Example 15 | Experimental Example 16 | Experimental Example 17 | Experimental Example 18 | Experimental Example 19 |
| --- | --- | --- | --- | --- | --- | --- | --- |
| Spraying Condition | Average Particle Diameter of Powder Spray Material (μm) | 30 | 30 | 20 | 20 | 10 | 10 |
|  | Distance W (mm) | 150 | 200 | 150 | 200 | 150 | 150 |
|  | Applied Voltage (V) | 70 | 70 | 70 | 70 | 70 | 80 |
|  | Current (A) | 500 | 500 | 500 | 500 | 500 | 600 |

TABLE 3-continued

|  |  | Experimental Example 14 | Experimental Example 15 | Experimental Example 16 | Experimental Example 17 | Experimental Example 18 | Experimental Example 19 |
|---|---|---|---|---|---|---|---|
| Measurement Result | Number of Interfaces in Unit Thickness Direction | 10 | 14 | 17 | 19 | 35 | 45 |
|  | Number of Interfaces in Unit Surface Direction | 13 | 11 | 10 | 9 | 8 | 7 |
|  | Ratio of Number of Interfaces | 1.30 | 0.79 | 0.59 | 0.47 | 0.23 | 0.16 |
| Evaluation Result | Average Value of Amount of Waterproofing (μL) | 3.1 | 5.6 | 112 | 10.5 | 14.8 | 14.5 |
|  | Evaluation of Waterproofing Performance | X | X | ○ | ○ | ○ | ○ |

Experimental Examples 20 to 25

In Experimental examples 20 to 25, the sensor element 101 was produced in the same manner as Experimental examples 1 to 4, 7, and 9 except that the thickness of each of the porous protective layers 91*a* to 91*e* was 500 μm. The waterproofing performance of each of Experimental examples 20 to 25 was evaluated in the same manner as Experimental examples 1 to 9. Table 4 collectively shows the plasma spraying condition, measurement results, and evaluation results of each of Experimental examples 20 to 25. In Experimental examples 20 to 25, the thickness of the porous protective layer 91 was 500 μm and, therefore, the average values of the waterproofing performance were large on the whole as compared with Experimental examples 1 to 4, 7, and 9 in which the thickness was 100 μm. However, the waterproofing performance of the cases of Experimental examples 20 and 21, in which neither the first condition nor the second condition was satisfied, was poor. On the other hand, the waterproofing performance of the cases of Experimental examples 22 and 23 was good and the waterproofing performance of the cases of Experimental examples 24 and 25 was very good.

TABLE 4

|  |  | Experimental Example 20 | Experimental Example 21 | Experimental Example 22 | Experimental Example 23 | Experimental Example 24 | Experimental Example 25 |
|---|---|---|---|---|---|---|---|
| Spraying Condition | Average Particle Diameter of Powder Spray Material (μm) | 30 | 30 | 20 | 20 | 10 | 10 |
|  | Distance W (mm) | 150 | 200 | 150 | 200 | 150 | 150 |
|  | Applied Voltage (V) | 70 | 70 | 70 | 70 | 70 | 80 |
|  | Current (A) | 500 | 500 | 500 | 500 | 500 | 600 |
| Measurement Result | Number of Interfaces in Unit Thickness Direction | 10 | 14 | 17 | 19 | 35 | 45 |
|  | Number of Interfaces in Unit Surface Direction | 13 | 11 | 10 | 9 | 8 | 7 |
|  | Ratio of Number of Interfaces | 1.30 | 0.79 | 0.59 | 0.47 | 023 | 0.16 |
| Evaluation Result | Average Value of Amount of Waterproofing (μL) | 9.5 | 9.8 | 16.8 | 18.2 | 30 | 30 |
|  | Evaluation of Waterproofing Performance | X | X | ○ | ○ | ◎ | ◎ |

The present application claims priority from Japanese Patent Application No. 2014-245661 filed on Dec. 4, 2014, and Japanese Patent Application No. 2015-233562 filed on Nov. 30, 2015, the entire contents of which are incorporated herein by reference.

What is claimed is:
1. A gas sensor element comprising:
an element main body including an oxygen ion-conductive solid electrolyte layer; and
a protective layer covering at least part of the element main body,
wherein a value of a number of interfaces in a measurement region of the protective layer in a thickness direction of the solid electrolyte layer, which is a value obtained by subtracting 1 from a number of constituent particles in the measurement region that intersect a base line drawn in the thickness direction, is greater than or equal to 15 and less than or equal to 250, and
wherein when a thickness of the protective layer is 100 μm or more in the thickness direction, the measurement region is a region of 100 μm in the thickness direction, and when the thickness of the protective layer is less than 100 μm in the thickness direction, the measurement region is an entire thickness of the protective layer, and the value of the number of interfaces in the measurement region is converted to a value corresponding to a measurement region thickness of 100 μm.
2. A gas sensor element comprising:
an element main body including an oxygen ion-conductive solid electrolyte layer; and
a protective layer covering at least part of the element main body,
wherein the protective layer includes a measurement region extending 100 μm in a surface direction of the solid electrolyte layer and up to 100 μm in a thickness direction of the solid electrolyte layer, the surface direction being perpendicular to the thickness direction, and a value of a ratio of a number of interfaces in the surface direction of the measurement region, which is a value obtained by subtracting 1 from a number of particle interfaces of constituent particles in the measurement region that intersect a first base line drawn in the surface direction, to a number of interfaces in the thickness direction of the measurement region, which is a value obtained by subtracting 1 from a number of particle interfaces of constituent particles in the mea- surement region that intersect a second base line drawn in the thickness direction, of greater than 0 and less than or equal to 0.7, and wherein when a thickness of the protective layer is 100 μm or more in the thickness direction, the measurement region is a region extending 100 μm in the thickness direction, and when the thickness of the protective layer is less than 100 μm in the thickness direction, the measurement region is an entire thickness of the protective layer, and the value of the number of interfaces in the thickness direction of the measurement region is converted to a value corresponding to a measurement region thickness of 100 μm.

3. The gas sensor element according to claim 1, wherein the value of the number of interfaces in the measurement region of the protective layer is 30 or more.

4. The gas sensor element according to claim 2, wherein the value of the ratio is 0.4 or less.

5. The gas sensor element according to claim 2, wherein the value of the ratio is 0.3 or less.

6. The gas sensor element according to claim 1, wherein a thickness of the protective layer is 500 μm or less.

7. The gas sensor element according to claim 2, wherein a thickness of the protective layer is 500 μm or less.

8. The gas sensor element according to claim 1, wherein the protective layer contains ceramic particles as the constituent particles.

9. The gas sensor element according to claim 2, wherein the protective layer contains ceramic particles as the constituent particles.

10. The gas sensor element according to claim 1, wherein the protective layer contains particles of at least one of alumina, zirconia, spinel, cordierite, titania, and magnesia as the constituent particles.

11. The gas sensor element according to claim 2, wherein the protective layer contains particles of at least one of alumina, zirconia, spinel, cordierite, titania, and magnesia as the constituent particles.

12. The gas sensor element according to claim 1,
wherein the element main body has long lengths of rectangular parallelepiped shape, and
the protective layer covers one end surface in a longitudinal direction of the element main body and regions of four surfaces perpendicular to the one end surface to the position at a distance L in the longitudinal direction of the element main body from the one end surface side (where 0<distance L<length in the longitudinal direction of the element main body).

13. The gas sensor element according to claim 2,
wherein the element main body has long lengths of rectangular parallelepiped shape, and
the protective layer covers one end surface in a longitudinal direction of the element main body and regions of four surfaces perpendicular to the one end surface to the position at a distance L in the longitudinal direction of the element main body from the one end surface side (where 0<distance L<length in the longitudinal direction of the element main body).

14. A gas sensor comprising the gas sensor element according to claim 1.

15. A gas sensor comprising the gas sensor element according to claim 2.

* * * * *